United States Patent [19]
Jaffe et al.

[11] Patent Number: 5,124,340
[45] Date of Patent: Jun. 23, 1992

[54] USE OF CALCIUM CHANNEL BLOCKER TO PREVENT COCAINE INDUCED CRAVING AND REINFORCEMENT

[75] Inventors: Jerome H. Jaffe; Karen Kumor, both of Baltimore, Md.

[73] Assignee: The United States of America as represented by the Department of Health and Human Services, Washington, D.C.

[21] Appl. No.: 372,607

[22] Filed: Jun. 28, 1989

[51] Int. Cl.$^5$ .................. A61K 31/445; A61K 31/44
[52] U.S. Cl. .................................. 514/356; 514/322; 514/812
[58] Field of Search ............... 514/279, 821, 812, 279, 514/356, 322

[56] References Cited

U.S. PATENT DOCUMENTS 4,797,410  1/1989  El-Fakahany .................... 514/356

OTHER PUBLICATIONS

Barrios et al. "Differential effects of calcium channel blockers and stimulants on morphine withdrawal in vitro" Eur. J. Pharmac. 152(88) 175-178.

Chem. Abst., 105-90819n (1986).

Snyder et al., Calcium-Antagonist Drugs, 1988, N. Engl. J. Med., pp. 995-1002.

Nahas et al., Calcium-Channel Blocker as Antidote to Cardiac Effects of Cocaine Intoxication, 1988, N. Engl. J. Med., pp. 519-520.

Miller, Multiple Calcium Channels and Neuronal Function, 1987, Science, pp. 46-52.

Rowbotham et al., Cocaine-Calcium Channel Antagonist Interactions, 1987, Psychopharmacology, pp. 152-154.

Primary Examiner—Frederick E. Waddell
Assistant Examiner—Diane Gardner
Attorney, Agent, or Firm—Birch, Stewart, Kolasch & Birch

[57] ABSTRACT

A method of treating cocaine addiction by administering to a patient in need thereof, an anti-cocaine addicting effective amount of a calcium channel blocking agent.

19 Claims, 4 Drawing Sheets

FEEL GOOD SCALE

GENERAL DRUG EFFECT SCALE

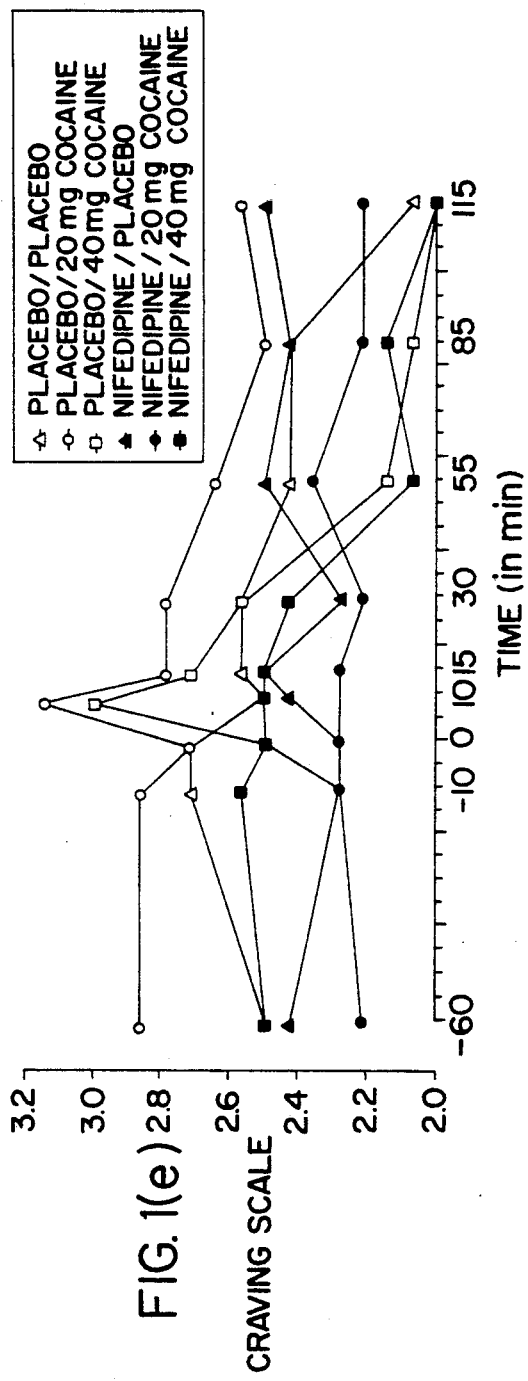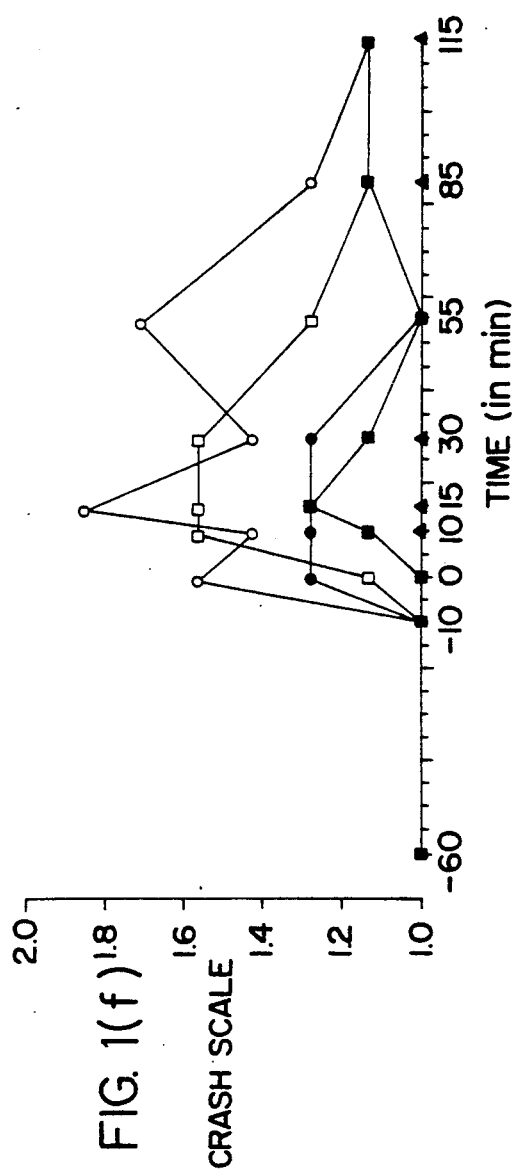

USE OF CALCIUM CHANNEL BLOCKER TO PREVENT COCAINE INDUCED CRAVING AND REINFORCEMENT

BACKGROUND OF THE INVENTION

The use of cocaine has been associated with the occurrence of functional and morphological-cardiovascular disorders such as cardiac arrhythmias and acute myocardial infarction, myocarditis and sudden death by Creglar and Mark, N. Engl. J. Med. 315:1495-1500 (1986).

Recent animal studies on the interaction between nitrendipine, a $Ca^{2+}$ modulator, and the cardiac effects of cocaine as reported by Nahas and Trouve, N. Engl. J. Med. 313:519-520 (1988), suggest that these drugs may antagonize the cardiac toxicity associated with cocaine use in humans.

The present inventors have studies the effects of calcium channel blockers, such as nifedipine, and have determined that these pharmacological agents reduced the subjective effects of cocaine including euphoria, "rush" and "craving" for cocaine in cocaine drug abusers. Euphoria is measured by scales designed to detect the mood elevating effects of a drug. "Rush" is an intense pleasurable sensation reported by drug users immediately after intravenous injection or inhalation of either cocaine or opioids. "Craving" is a sense of wanting or needing to use the drug again and is measured in these studies by asking the subject to report on the intensity of this urge to use. Thus, the present invention has been accomplished with the above problems in mind.

SUMMARY OF THE INVENTION

The present invention is directed to a method of treating cocaine addiction by administering to a patient in need thereof an effective amount of a calcium channel blocking agent, in order to reduce the abusers craving for cocaine.

The present invention is also directed to a method for the prophylactic treatment of cardiac toxicity due to cocaine by administering an anti-cocaine cardiotoxic effective amount of a calcium channel blocking agent.

By calcium channel blocking agent is meant any agent which blocks movement of calcium through calcium channels in cell membranes. Of these agents, the dihydropyridine class of calcium channel blockers are preferred. Examples of these agents and where they can be obtained are nifedipine from Pfizer, Inc., nitrendipine from Miles Pharmaceuticals, nimodepine from Miles Pharmaceuticals, nicardipine from Syntex Laboratories, Inc., nisoldipine from Miles Pharmaceuticals, Bay K 8644 from Miles Pharmaceuticals, verapamil from Searle and Co., isradipine from Sandoz Pharmaceuticals Corp., felodipine from Astra Pharmaceutical Products, Inc., and tiapimal from Hoffman LaRoche, Inc.

These agents can be administered prior to, during, and after cocaine use. Preferably these agents are administered on a regular basis until risk of relapse is low, preferably for a period of about 8-16 weeks.

In the case of when nifedipine is employed in the method of the present invention, appropriate doses can be from 0.5 mg/kg-1.5 mg/kg body weight, per day. More preferred doses for the present method are 30 to 90 mg per day. A preferred dosage regimen is from about 10 to 30 mg, three times a day. For calcium channel blockers other than nifedipine, the dosage can suitably be determined by one skilled in the art and can be chosen from the same ranges indicated for other therapies reported in the literature and/or Physicians Desk Reference. Useful doses of the calcium channel blocking agents utilized in the methods of the present invention fall within the range of about 0.01 to 100 mg/kg body weight per day.

The calcium channel blockers which are utilized in the method of the present invention may be administered in pharmaceutical compositions by combination with appropriate medical carriers or diluents, and may be formulated into preparations in solid, semisolid, liquid or gaseous forms such as tablets, capsules, powders, granules, ointments, solutions, suppositories, injections, inhalants, aerosols in usual ways for oral or parenteral administration. These formulations can include sustained release formulations and can be readily prepared by those skilled in this art. The following methods and excipients are merely exemplary and are in no way limiting.

In pharmaceutical dosage forms, the calcium channel blockers may be used in the form of their pharmaceutically acceptable salts, and also may be used alone or in appropriate association, as well as in combination with other pharmaceutically active compounds.

In the case of oral preparations, the calcium channel blockers may be used alone or combined with appropriate additives to make tablets, powders, granules or capsules, e.g. with conventional additives such as lactose, mannitol, corn starch or potato starch; with binders such as crystalline cellulose, cellulose derivatives, acacia, corn starch, potato starch or sodium carboxymethylcellulose; with lubricants such as talc or magnesium stearate; and if desired, with diluents, buffering agents, moistening agents, preservatives and flavoring agents.

Furthermore, they may be made into suppositories by mixing with a variety of bases such as emulsifying bases or water-soluble bases.

The calcium channel blockers may be formulated into preparations for injections by dissolving, suspending or emulsifying them in aqueous solvents such as normal saline, Dextrose 5%, or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In case of inhalations or aerosol preparations, the calcium channel blockers in the form of a liquid or minute powder may be filled up in an aerosol container with gas or liquid spraying agents, and if desired, with conventional adjuvants such as humidifying agents added. They may also be applied as pharmaceuticals for non-pressurized preparation such as in a nebulizer or an atomizer.

In the case of sustained release formulations, osmotic pumps are a preferred mode of administration. Osmotic pumps are drug formulations which absorb fluid from, e.g., the intestinal tract or subcutaneously. As a result of the absorption of fluid, reservoirs which hold the drug are compressed, thus causing the controlled release of the drug.

BRIEF DESCRIPTION OF THE DRAWINGS

FIGS. 1a-f depict the effects of oral nifedipine pretreatment on responses to cocaine injections as a function of time during experimental sessions. Each point represents the mean for seven subjects. Mean scale scores are shown for the General Drug Effect, Feel Good scales. Scores could range between 1 and 5. Nifedipine or placebo was administered 20 min before cocaine or placebo (abscissae time 0).

DETAILED DESCRIPTION OF THE INVENTION

Figure 1A:
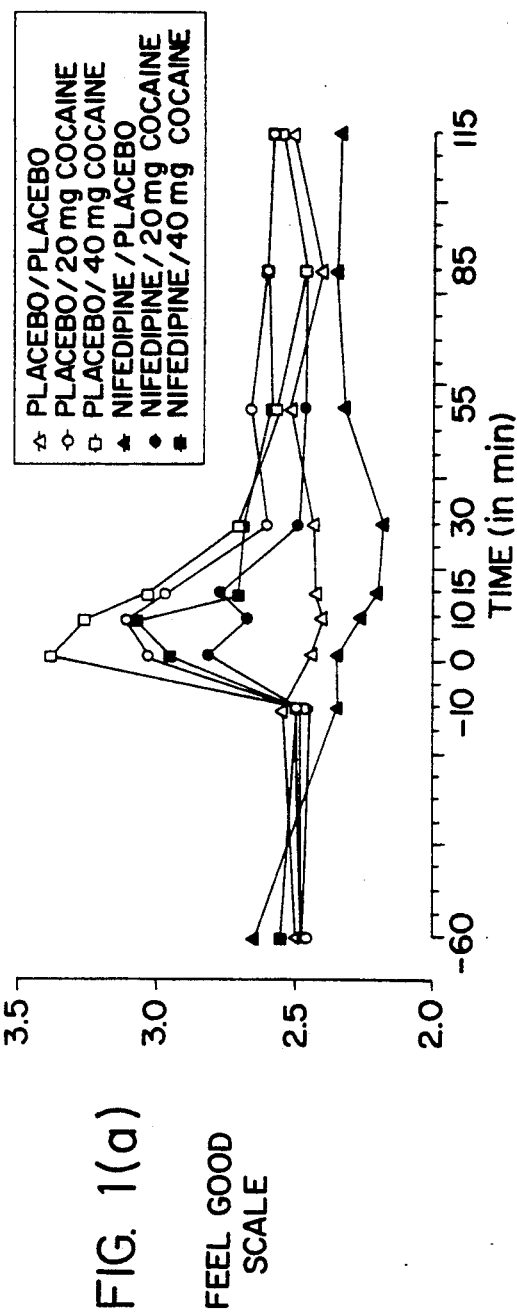

The following invention will be discussed in greater detail hereinbelow. All percentages are by weight unless expressly stated to the contrary.

EXAMPLE

Effect of Nifedipine on Cocaine Addiction Materials and methods

Subjects

Seven male volunteers, 27–42 years old (mean age 34 years), participated in the study approved by the Institutional Review Board of the Francis Scott Key Medical Center; written informed consent was obtained from all subjects. Initial criteria for subject selection required a history of recent intravenous cocaine use and passage of the vocabulary part of the Shipley-Hartford Retreat Scale with a minimum mental age score of 12.3 (Shipley, 1940). Subjects were also required to be HIV antibody negative, pass physical and laboratory screening tests, including EKG, and not fulfill criteria for current DSM III Axis I (APA, 1980) disorders other than substance abuse disorders. Subjects were admitted to a closed research ward, and random urine screens were performed throughout the study period to ensure that subjects were exposed only to those substances administered as part of the research protocol. Following admission to the ward, the nursing staff observed subjects for signs and symptoms of sedative or opiate withdrawal. None of the study subjects exhibited signs of withdrawal or illicit drug use during the 3-day minimum baseline washout period.

After medical evaluation, subjects were tested for unusual sensitivity to cocaine using a series of single i.v. infusions of cocaine. Doses of placebo and 10, 20, and 40 mg of cocaine were delivered in a pseudo-randomized order under double-blind conditions, such that the 20 mg dose of cocaine was always scheduled before the 40 mg dose. A minimum of 24 hours elapsed between test doses. During this preliminary safety testing, cardiac function was monitored by EKG. On the basis of this preliminary testing, two research volunteers were rejected for further study due to unusual cardiovascular reactivity. One subject withdrew for personal reasons.

Subjects' psychiatric status were assessed with the National Institute of Mental Health Diagnostic Interview Schedule (NIMH-DIS; Robins et al., 1980) adapted for computer administration. Two subjects had a history of major depressive disorders. Within the substance abuse disorders, 5 subjects had a history of alcohol dependence, 5 of tobacco dependence, 2 of barbiturate dependence, and 4 of opioid dependence. Finally, 3 subjects had a history of cannabis abuse and 3 of cocaine abuse. Two subjects had a history of antisocial personality disorder, with three having features of this diagnosis, and one subject had a history of pathological gambling. The seven selected subjects had used i.v. cocaine within the three weeks prior to participating in the study. All subjects had a history of alcohol, tobacco, opioid, and cannabis use.

Procedure

After successful completion of the safety screening, subjects participated in the study and received six different experimental drug conditions presented in a randomly determined order. These conditions were: (1) placebo oral pretreatment followed by placebo i.v. administration, (2) placebo oral pretreatment followed by 20 mg i.v. cocaine administration, (3) placebo oral pretreatment followed by 40 mg i.v. cocaine administration, (4) 10 mg nifedipine obtained from oral pretreatment followed by placebo i.v. administration, (5) 10 mg nifedipine oral pretreatment followed by 20 mg i.v. cocaine administration, and (6) 10 mg nifedipine oral pretreatment followed by 40 mg i.v. cocaine administration.

Experimental sessions were scheduled no more frequently than every 48 hours. Each session was conducted under double-blind conditions in the same sound-insulated room. A physician, and sometimes two physicians were present during the first hour of the experiment. Two research nurse/technician observers were always present throughout the study period. Observers refrained from talking with each other or initiating conversation with the subjects and provided a supportive but non-directive milieu in their interactions with the subjects. Cardiac function was continually monitored prior to and for the first 30 min after the i.v. infusion; it was monitored periodically thereafter. Intervention protocols were in place to respond in the event of medical emergencies.

On each study day, following an overnight fast and a standard breakfast, an indwelling i.v. heparin-lock catheter was inserted into a forearm vein and flushed with heparinized saline 60 minutes before receiving the infusion. Subjects reclined in bed during the sessions. Oral pretreatments with nifedipine 10 mg or placebo (lactose) were administered in identical gelatine capsules 20 min before the beginning of the infusion. Cocaine or placebo (saline) infusions were administered using a pressure pump (Sage instruments Syringe Pump model 341) which infused drug into the indwelling catheter via a needle inserted into the heparin lock. Either cocaine or saline was infused over a period of 12 sec. The start of the infusion was determined by a computer which was programmed to activate the pump randomly during a 5 min interval after the attending physician pressed a start key. No visual or auditory cues indicated the moment in which the infusion started, a "beep" sounded 2 min after the end of the infusion. Subjects rested in bed during the 30 min following the infusion. Limited ambulation was allowed thereafter, but subjects were not permitted to exercise.

Measures

Blood pressure and heart rate were measured at 60 and 10 minutes before the infusion and 2, 10, 15, 30, 55, 85, and 115 minutes after the infusion. Systolic and diastolic blood pressure and heart rate were sampled via a BARD Biomedical Sentron automated blood pressure monitor. Cardiac monitors could not be seen by the subjects.

SELF REPORT RATING SCALES

A computer-administered 30-item rating scale was used as a measure of the subjective effects produced by i.v. cocaine administration. The items were rated on a five point scale (1=not at all, 2=a little bit, 3=average, 4=quite a lot, 5=extremely). Principal components analysis of the 30-item scale produced six subscales with high face validity. These subscales were labeled General Drug Effect (8 items: "How confused does the drug make you feel?," "How much rush do you feel?," "How anxious do you feel?", "How confused do you feel?," "How weird do you feel?", "How much do you feel the drug?", "How high do you feel?", "How anxious does the drug make you feel?", Feel Good (5 items: "How good do you feel?", "How clear is your thinking?", "How good does the drug make you feel?", "How pleasant do you feel?"), Suspiciousness (3 items: "How suspicious do you feel?", "Can the staff tell what you are thinking?", "How uncomfortable do you feel?"), Craving (2 items: "How much do you need cocaine?", "How much do you want cocaine?"), Sexual Arousal (2 items: "How sexy do you feel?", "How powerful do you feel?", and Crash (1 item: "How much crash do you feel?"). This 30 item rating scale was used during the first 15 min after the injection because it permitted frequent measurements of cocaine-relevant subjective effects over the brief peak of cocaine addiction. Subjects made their ratings by using an arrow key controlling the cursor. The scale was administered at 60 and 10 min before the beginning of the infusion and at 2, 10, 15, 30, 55, 85, 115 min after the infusion.

A 10-point computer administered bar-graph (Rush-graph) was used to measure the euphoric subjective effect sometimes termed "rush". According to the following, a series of interval scales to provide additional measures of sensations commonly reported as effects of cocaine were used. Among areas probed by these interval scales are self-rated feelings. Included among these was one scale labeled as "rush". These items were selected following a perusal of the literature and interviews with intravenous cocaine users. All the cocaine-sensitive interval scale (CSI) items were subjected to pilot testing in between 3-5 cocaine users (different from study subjects) using doses of 10 to 80 mg of intravenous cocaine prior to a double-blind cross-over experiment. The scales were scored only as face value measures and no effort was made to remove redundant or covariant dimensions of the scales. The CSI scales were presented to the subject on a computer display terminal as a horizontal line labeled from 0-9 at evenly spaced intervals. Subjects selected the desired rating by use of the computer number pad. In addition, to the horizontal CSI scale for measuring "rush," the sensation "rush," was also assessed by allowing the subjects to rate themselves on a computerized bar graph. Subjects adjusted a cursor on the ordinate for "rush" intensity, causing a thick line on the computer monitor to be generated parallel to the ordinate. After each rating, the cursor automatically shifted to the next point on the abscissa. At the next timepoint for self-rating, the subject was able to view his previous response(s), and then adjust the cursor to correspond to his current rating of the intensity of "rush." Thus, the subjects developed and responded to a histogram-like graph of "rush" (graphic rush). In this histogram of intensity versus time the ordinate measuring intensity was labeled as a 100-point scale, the abscissa was labeled "time." "Rush" has a rapid onset and a brief duration after i.v. cocaine administration. Subjects rated "rush" on the bar-graph each time they completed the 30-item rating scale.

A computer-administered form of the Profile of Mood States POMS as disclosed by McNair et al., Manual for the Profile of Mood States, Educational and Industrial Testing Service, San Diego, 1971 consisted of sixty-five adjectives commonly used to describe transient mood states. For each item, subjects indicated how they felt at the moment according to a five-point rating scale (0=not at all, 1=a little, 2=moderately, 3=quite a bit, 4=extremely). Subjects made their ratings by using the arrow key controlling the cursor. The POMS includes six scales (Tension-Anxiety, Depression-Dejection, Anger-Hostility, Vigor-Activity, Fatigue-Inertia, and Confusion-Bewilderment), with between seven and fifteen items comprising each scale. The score on each scale is obtained by adding the numbers checked on each item. The POMS was administered at 60 min before the infusion and at 15, 60, 90, and 120 min after the infusion.

OBSERVERS' QUESTIONNAIRES AND RATING SCALES

Two observers rated the subjects using the Single Dose Questionnaire for Observers as disclosed by Haertzen, Advances in Biochemical Psychopharmacology, Vol. 8, New York, Raven, pp. 383-398, 1974, which has previously been used in studies of opiate effects. The Single Dose Questionnaire is a checklist that includes items of behaviors commonly observed after opiate administration. Observers were required to check if there was any evidence of drug effect and if the behavior was like that seen after cocaine. Then observers were required to check if they observed any of 14 items such as "relaxed," "high," "nervous," "coasting," or "need to talk." Finally, the observers were asked to rate the subjects' liking for the drug on a five-point rating scale (1=not at all, 2=slight, 3=moderate, 4=a lot, 5=an awful lot). Preliminary analyses showed that there was little response to drug conditions on most items; however, there were three items, for which scores varied among conditions; "Is the behavior observed like that seen after cocaine?," "high," and "liking." These three variables were analyzed separately.

Observations on the ARCI Single Dose Questionnaire were scheduled at 5 min before the infusion and 5, 15, 30, and 55 min after the infusion. Overall, there was good agreement between the two observers across conditions, with correlations ranging from 0.70 to 0.90. Scores for the two observers were therefore averaged for the present analyses.

Data analyses

Three-way repeated measures analyses of variance (ANOVA) followed by post-hoc paired t-tests were performed. The main factors in the analysis were the pretreatment condition (nifedipine or placebo), cocaine dose (placebo, 20 mg, or 40 mg), and the time points. In order to protect the experiment-wise error rate only five sampling times were used in the ANOVAs ($-10$, and $+2$, $+15$, $+30$, and $+55$ min relative to the injection).

Results

Cardiovascular measures

Heart rate increases after cocaine infusion were lowered by nifedipine pretreatment, as indicated by the significant interactions of drug condition of time [$F(4,24) = 2.92$, $p < 0.05$] and near-significant interaction of drug condition by dose of cocaine by time [$F(8,48) = 2.02$, $p = 0.06$] on heart rate. The latter result suggests that nifedipine was particularly effective in blocking cocaine-induced increases in heart rate for the 40 mg dose.

Paired t-tests on the change scores from baseline (10 min before the infusion) to the 2 min post-infusion values were conducted to compare corresponding placebo v. nifedipine pretreatment conditions. None of these tests achieved statistical significance.

SELF-REPORT RATING SCALES

Cocaine produced dose-dependent increases in the General Drug Effect [$F(2,12) = 26.99$, $p < 0.001$], Feel Good [$F(2,12) = 10.25$, $p. < 0.004$], and Crash [$F(2,12) = 6.33$, $p < 0.02$] scale as shown in FIG. 1 scores. For the Craving and Crash scales, the effects of 20 mg cocaine were greater than for 40 mg. Peak effects were observed at 2 min post infusion for General Drug Effect, Feel Good, and Sexual Arousal scores. Peak effects were observed at 15 min post infusion for Suspiciousness, Craving, and Crash scores as shown in FIGS. 1d–f, respectively. The scores for Suspiciousness, Sexual Arousal as shown in FIG. 1c, and Craving returned to baseline approximately one hour after injection. Two hours after the infusion, General Drug Effect and Feel Good scores had returned to baseline, while Crash scores remained above baseline levels.

Main effects for time (changes in scores over time) were present on the General Drug Effect [$F(4,24) = 31.31$, $p < 0.001$] and Feel Good [$F(4,24) = 4.59$, $p < 0.006$] and Suspiciousness [$F(4,24) = 4.30$, $p < 0.008$] scales.

Nifedipine pretreatment decreased scores on the Sexual Arousal [$F(1,6) = 7.35$, $p < 0.04$] and Craving [$F(1,6) = 5.68$, $p < 0.05$] scores compared with placebo pretreatment. This non specific effect was evident at the −10 minutes between baseline measurements. These data suggest that nifedipine may have intrinsic psychopharmacologic effects in this population.

Figure 1B:
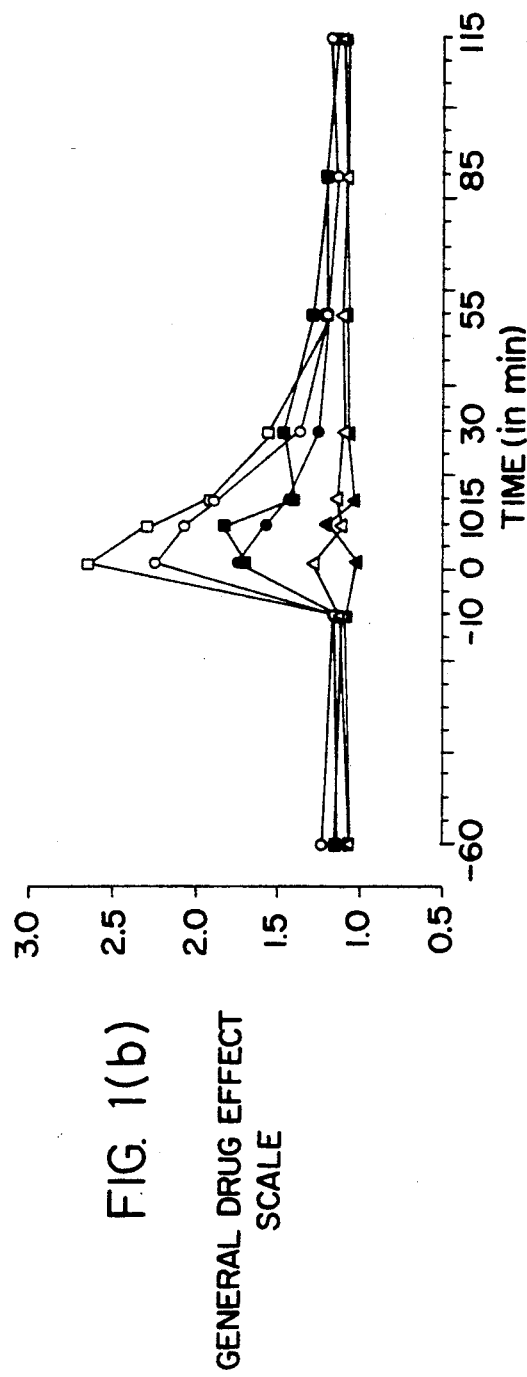
Figure 2A:
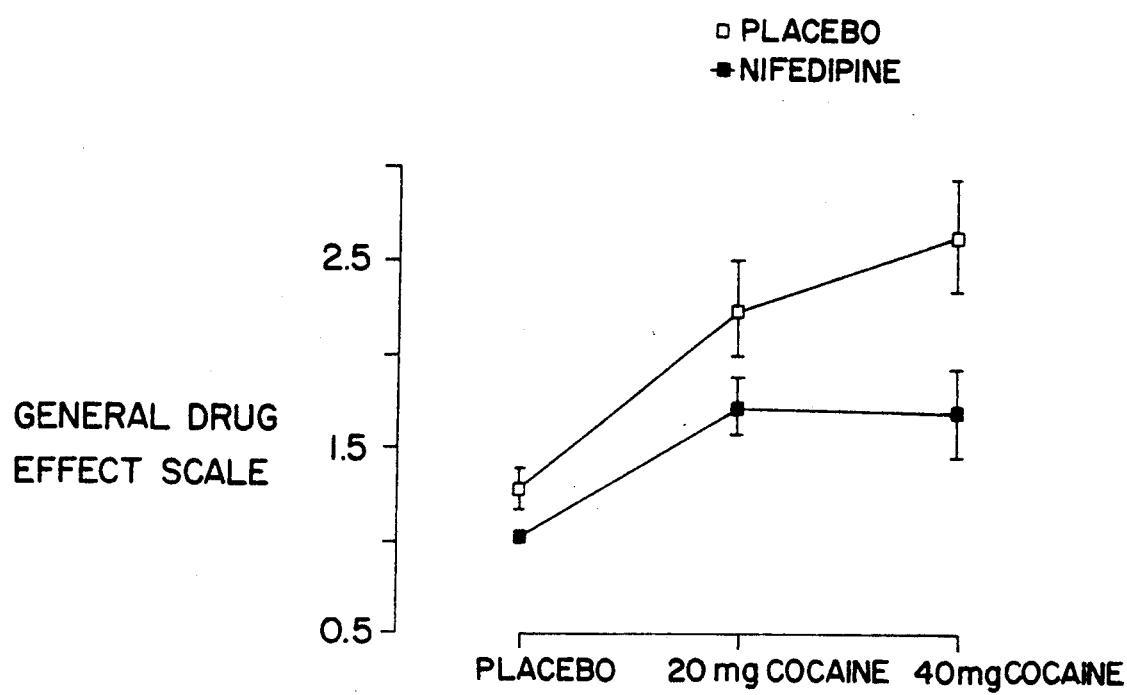
FIGS. 2a and 2b depict the mean values of General Drug Effect and Feel Good scales 2 min after the injection.
Figure 2B:
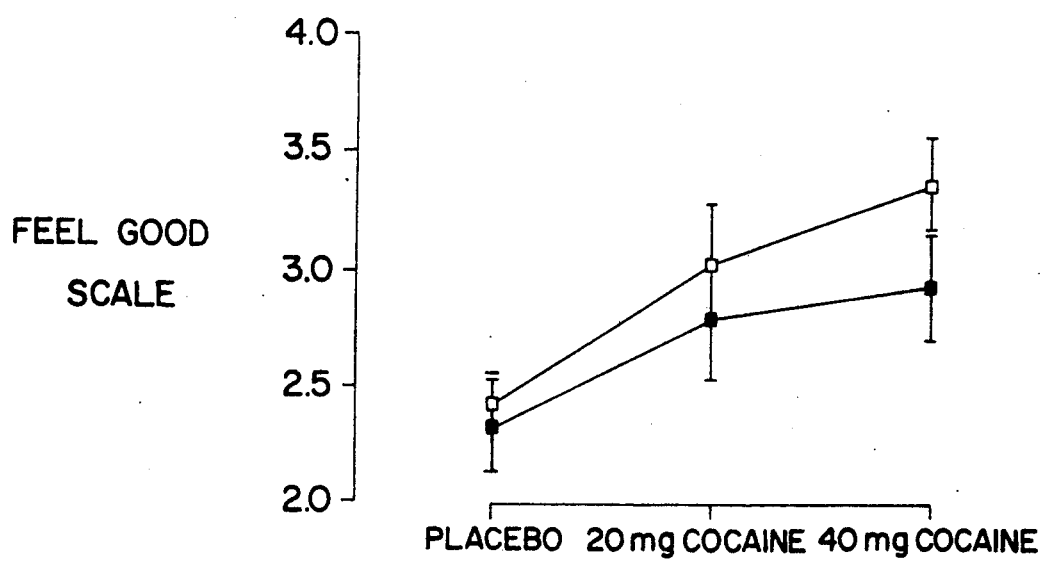

As can be seen from FIGS. 1a and 1b, nifedipine pretreatment also attenuated cocaine-induced increases on the scores for the General Drug Effect and Feel Good scales. The peak effect of nifedipine on these scales occurred at 2 min after the cocaine injections which is also the time of maximum cocaine effect. The ANOVA results supporting this interpretation are the significant interaction of drug pretreatment condition (nifedipine vs. placebo pretreatment) and time [$F(4,24) = 6.56$, $p,0.002$], and drug pretreatment condition by dose of cocaine by time [$F(8,48) = 2.50$, $p < 0.03$] on the General Drug Effect Scores. For the Feel Good Scale the interaction of drug pretreatment condition (nifedipine vs placebo) by cocaine dose by time missed statistical significance [$F(8,48) = 1.47$, $p < 0.19$] but had a trend compatible with a reduction of cocaine-induced scores by nifedipine. The presence of the significant interaction on the General Drug Effect Scale for the drug pretreatment with the cocaine dose and time reveals that the blockade of cocaine-induced effects by nifedipine is a function of dose and is more intense at the 40 mg dose of cocaine. The mean dose response data for the peak scores occurring at two minutes for the General Drug Effect and Feel Drug Scales are presented in FIGS. 2a–b.

Figure 1C:
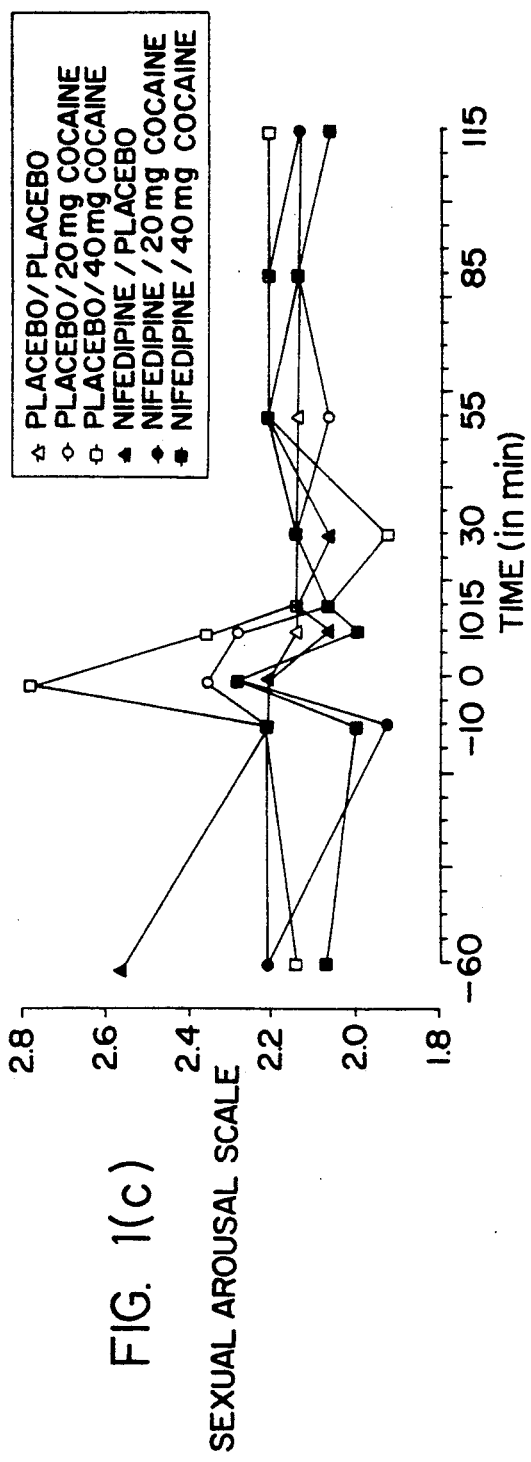
Figure 1D:
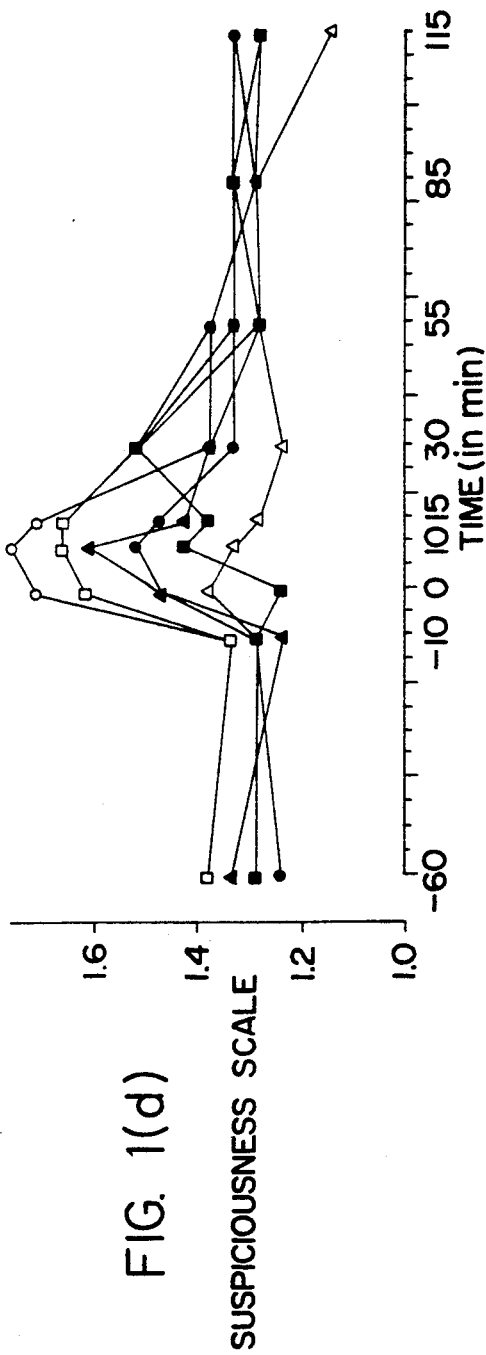

Post-hoc paired t-tests conducted on the change-scores for the General Drug Effect Scale (10 min before injection to 2 min post-injection) revealed two significant differences between treatment conditions: between the placebo and nifedipine pretreatments for the cocaine 40 mg injection conditions [paired $t = 2.76$, $p < 0.04$] and between placebo and nifedipine pretreatments for the placebo injection condition [paired $t = 2.65$, $p < 0.04$]. Since mean baseline scores for the conditions are nearly identical as seen in FIGS. 1a–c, these analyses imply that nifedipine blocks both cocaine-induced increase in scores on the General Drug Effect Scale and, furthermore, that nifedipine blocks the small rise in scores observed after injection of placebo; that is, blocks the placebo effect.

During the placebo pretreatment conditions, seven subjects reported the presence of rush using the Rushgraph after injections of 40 mg of cocaine and six reported it after the 20 mg dose of cocaine. Three subjects reporting rush after both cocaine 20 and 40 mg reported not experiencing rush at either dose of cocaine given after the nifedipine pretreatment. The other three subjects reported no change between their scoring of the two cocaine doses in the presence or absence of nifedipine. One subject rated the rush after 40 mg of cocaine with a nifedipine pretreatment as diminished in intensity compared the placebo pretreatment. This subject reported having no rush after the 20 mg of injections of cocaine. The ANOVA shows that there was a significant interaction for pretreatment condition by cocaine dose by time for the Rushgraph Scale scores, supporting the interpretation that rush was significantly reduced after nifedipine pretreatment in our experiment [$F(8,48) = 3.14$, $p < 0.006$]. The ANOVA for the interaction of pretreatment condition with time was also significant [$F(4,24) = 6.02$, $p < 0.16$]. The results of the "rush" question included on the General Drug Effect Scale was also analyzed separately. These results were completely in agreement with the results of the Rushgraph Scale scores.

Analyses of the POMS data were generally concordant with the results obtained by the General Drug Effect Scale. Pretreatment with nifedipine significantly attenuated the cocaine-induced responses on the POMS Confusion [$F(4,24) = 7.09$, $p < 0.001$] and Tension Scales [$F(4,24) = 2.75$, $p = 0.05$] as shown by the significant interactions of the drug pretreatment by dose by time.

The peak activity of nifedipine on these scales appeared 15 minutes after the cocaine injections. However, the nifedipine had no overall effect (main effect of pretreatment) on the POMS scores. On this widely used general purpose scale, nifedipine, in contrast to the 30 item scale, did not demonstrate activity in the absence of cocaine before injections. Post hoc t-tests of the 15 minute post-injection scores produced a significant difference on the Confusion Scale (paired $t = 3.04$, $p < 0.03$) between the two pretreatment conditions, nifedipine and placebo, given prior to the 40 mg dose of cocaine and narrowly missed significance on the Tension Scale (paired $t = 2.26$, $p < 0.07$).

OBSERVERS' QUESTIONNAIRES AND RATINGS SCALES

Nifedipine had a significant overall main effect on scores from the Single Dose Questionnaire for the reporting of "cocaine-like behavior" [$F(1,6)=18.15$, $p<0.004$] and "high" [$F(2,12)=19.44$, $p<0.002$] items. This result is similar to the results for the Sexual Arousal and Craving Scales in that the effect is present even in the absence of cocaine at baseline or after placebo injections. The comparison of the 5-minute pre-injection scores of the pretreatment conditions, nifedipine and placebo, were nearly significantly different for cocaine identification (paired t-test $=2.12$, $p=0.08$) and "high" (paired $t=1.92$, $p=0.1$). It is possible that observers could detect the presence of nifedipine alone. However, there were no significant interactions between the drug pretreatment condition with the cocaine dose or time for measures of "behavior like cocaine", "high" and "liking". Therefore, nifedipine did not clearly demonstrate an ability to reduce the observer ratings of cocaine-induced effects for these measures. This finding is concordant with a similar finding observed for the Cocaine Observers Scale.

The paired t-test of the observer "liking" scores comparing the two pretreatment conditions for a 40 mg dose of cocaine were nearly significant (paired $t=1.90$, $p=0.11$). This strong trend suggests that observers were able to see some change or reduction in the pleasurable effects of cocaine following nifedipine pretreatment.

Nifedipine alone reduced scores on two subjective measures, Craving and Sexual Arousal, independent of cocaine dosing. This suggests that nifedipine alone may alter subjective states under some circumstances. It was also found that nifedipine attenuated the placebo induced increases in scores on the General Drug Effect scale and on the observers' ratings of "behavior like cocaine" and "high" from the Single Dose Questionnaire.

The experiment indicates that nifedipine pretreatment significantly attenuates cocaine induced increases in subjective effects, including scores on the General Drug Effect scales. Trends supportive of nifedipine blockade of cocaine effects were also observed on the Feel Good scale, and the Observer's Single Dose Questionnaire.

Having thus described the invention, it is understood that the same may be varied in many ways. Such variations as they might readily occur to one skilled in the art, are not to be regarded as a departure from the spirit and scope of the invention, and all such modifications are intended to be included within the scope of the following claims.

We claim:

1. A method of treating cocaine addiction by administering to a patient in need thereof, an anti-cocaine addicting effective amount of a dihydropyridine calcium channel blocking agent.

2. The method according to claim 1 wherein said dihydropyridine is selected from the group consisting of nifedipine, nimodipine, nitrendipine, nilvadipine, nicardipine, nisoldipine, Bay K 8644, isradipine, and felodipine.

3. The method according to claim 1 wherein said calcium channel blocking agent is administered prior to, during, and after cocaine use.

4. The method according to claim 2 wherein said calcium channel blocking agent is nifedipine and said anti-cocaine addicting effective amount is 0.5 to 1.5 mg/kg/day.

5. The method according to claim 4 wherein said anti-cocaineXaddicting effective amount administered is 1 to 30 mg, three times a day.

6. The method according to claim 1 wherein said calcium channel blocking agent is administered orally.

7. The method according to claim 1 wherein said calcium channel blocking agent is administered parenterally.

8. The method according to claim 1 wherein said calcium channel blocking agent is administered by way of an osmotic pump.

9. The method according to claim 6 wherein said oral administration is by way of a sustained release formulation.

10. The method according to claim 1 wherein said calcium channel blocking agent is administered for a period of about 8-16 weeks.

11. A method for the prophylactic treatment of cardiac toxicity due to cocaine comprising administering to a patient in need thereof an anti-cocaine cardiotoxic effective amount of a dihydropyridine calcium channel blocking agent.

12. The method according to claim 11 wherein said dihydropyridine is selected from the group consisting of nifedipine, nimodipine, nitrendipine, nilvadipine, nicardipine, nisoldipine, Bay K 8644, isradipine, and felodipine.

13. The method according to claim 12 wherein said calcium channel blocker is nifedipine.

14. The method according to claim 13 wherein said anti-cocaine cardiotoxic effective amount is 0.5 to 1.5 mg/kg/day.

15. The method according to claim 13 wherein said anti-cocaine cardiotoxic effective amount administered is 1 to 30 mg, three times a day.

16. The method according to claim 11 wherein said calcium channel blocking agent is administered orally.

17. The method according to claim 11 wherein said calcium channel blocking agent is administered parenterally.

18. The method according to claim 11 wherein said calcium channel blocking agent is administered by way of an osmotic pump.

19. The method according to claim 16 wherein said oral administration is by way of a sustained release formulation.

* * * * *